United States Patent [19]

Rice

[11] Patent Number: 4,727,146
[45] Date of Patent: Feb. 23, 1988

[54] SYNTHESIS OF CHIRAL 1-BENZYL-1,2,3,4-TETRAHYDROISOQUINOLINES BY ASYMMETRIC REDUCTION

[75] Inventor: Kenner C. Rice, Rockville, Md.

[73] Assignee: The United States of America as represented by the Department of Health and Human Services, Washington, D.C.

[21] Appl. No.: 748,854

[22] Filed: Jun. 26, 1985

Related U.S. Application Data

[63] Continuation-in-part of Ser. No. 476,830, Mar. 18, 1983, Pat. No. 4,456,712, which is a continuation-in-part of Ser. No. 265,469, May 20, 1981, Pat. No. 4,410,700, which is a continuation-in-part of Ser. No. 165,690, Jul. 3, 1980, abandoned.

[51] Int. Cl.$^4$ .......................................... C07D 217/20
[52] U.S. Cl. ..................... 546/148; 546/44; 546/45; 546/146; 546/149
[58] Field of Search ............... 546/146, 149, 44, 45, 546/148

[56] References Cited

U.S. PATENT DOCUMENTS

| | | | |
|---|---|---|---|
| 3,849,480 | 11/1974 | Knowles et al. | 560/250 |
| 3,914,232 | 10/1975 | Mohacsi et al. | 546/146 X |
| 4,368,326 | 1/1983 | Rice | 546/45 |
| 4,410,700 | 10/1983 | Rice | 546/149 |
| 4,556,712 | 12/1985 | Rice | 546/149 |

FOREIGN PATENT DOCUMENTS

| | | | |
|---|---|---|---|
| WO82144 | 1/1982 | PCT Int'l Appl. | 546/74 |
| WO82/4049 | 11/1982 | PCT Int'l Appl. | 546/74 |

OTHER PUBLICATIONS

Achiwa, et al., Chemical Abstracts, vol. 88: 105618c (1978).
Rice, J. Organic Chem., vol. 45, No. 15, pp. 3135–3137 (07/18/80).
Yamada, et al., Chemical Abstracts, vol. 98(9):72505q (1983).
Hsu, et al., Hevetia Chimica Acta, vol. 63, No. 7, pp. 2042–2045 (10/29/80).
Noyori, et al., J. Am. Chem. Soc., vol. 108, No. 22, pp. 7117–7119 (1986).
Merrill, "Asymmetric Synthesis Using Chiral Phosphine Ligands," Reaction Design Corp., Hillside, NJ, 1980, pp. 1–87.
Brown, et al., Tetrahedron, vol. 37, pp. 3547–3587, 1981.
Yamaguchi et al, Yakugaku Zasshi, 82:552 (1962); abstracted in Optical Resolution Procedures for Chemical Compounds, vol. 1, Amines and Related Compounds, by Paul Newman, p. 398, Optical Resolution Ctr., Riverdale, NY.

Primary Examiner—Donald G. Daus
Assistant Examiner—Diana G. Rivers
Attorney, Agent, or Firm—John S. Roberts, Jr.

[57] ABSTRACT

In a short total synthesis of morphinan compounds, derivatives of 1-benzyl-1,2,3,4-tetrahydroisoquinoline are produced. Certain of these compounds, although highly aromatic and functionalized, can be optically resolved. The optically active enantiomers can serve as important intermediates for both natural and unnatural opioids. As a special function of this invention, certain of the derivatives, namely 4'–6' and 7'–9', may be hydrogenated to 1'–3' derivative by asymmetric reduction either of the catalytic or chemical type.

1 Claim, No Drawings

SYNTHESIS OF CHIRAL 1-BENZYL-1,2,3,4-TETRA-HYDROISOQUINO-LINES BY ASYMMETRIC REDUCTION

CROSS REFERENCE

This application is a continuation in part of pending U.S. Ser. No. 476,830 filed Mar. 18, 1983, which is a continuation in part of U.S. Ser. No. 265,469 filed May 20, 1981 (now U.S. Pat. No. 4,410,700), which is a continuation in part of U.S. Ser. No. 165,690 filed July 3, 1980, now abandoned.

MATERIAL INFORMATION DISCLOSURE

Merrill, "Asymmetric Synthesis Using Chiral Phosphine Ligands," Reaction Design Corporation, Hillside, NJ, 1980.

Brown, et al., "Asymmetric Synthesis Via Chiral Organoborane Reagents," *Tetrahedron*, Vol. 37, page 3547, 1981.

U.S. Pat. No. 3,849,480 Knowles et al

Ger. Offen, No. 2,456,937 Knowles et al

Yamaguchi et al, Yakugaku Zasshi, 82:552 (1962), abstracted in Optical Resolution Procedures for Chemical Compounds, Volume 1, Amines and Related Compounds, by Paul Newman, Optical Resolution Information Center, Riverdale, NY, page 398—the solvent and conditions for this isoquinoline differ substantially from the present invention.

BACKGROUND OF THE INVENTION

In a short total synthesis of morphinan compounds, derivatives of 1-benzyl-1,2,3,4-tetrahydroisoquinoline are produced. Certain of these compounds, although highly aromatic and functionalized, can be optically resolved. The optically active enantiomers can serve as important intermediates for both natural and unnatural opioids. As a special function of this invention, certain of the derivatives, namely, 4'-6' and 7'-9', may be hydrogenated to 1'-3' derivatives by asymmetric reduction either of the catalytic or chemical type.

The present application relates to production of chiral intermediates for total synthesis of (−)- and (+)-opioids. Since all medically important opium derivatives, including thebaine, can be manufactured from intermediates prepared in the above-mentioned disclosure, the simple and effective methods described below for synthesis of chiral precursors are of fundamental importance. In addition to affording intermediates for production of (−)-opiods (natural), the present disclosure also permits synthesis of intermediates useful for preparing (+)-opiods which are of importance as antitussive agents and neuropharmacological research tools.

The synthesis outlined for the total short synthesis of dihydrothebainone, dihydrocodeinone, and nordihydrododeinone is shown schematically in the following outline, Flow Diagram 1.

Flow Diagram 1
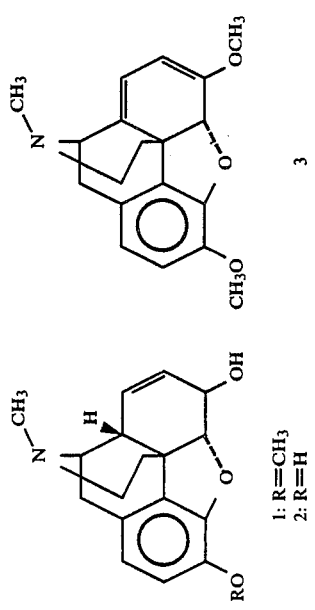
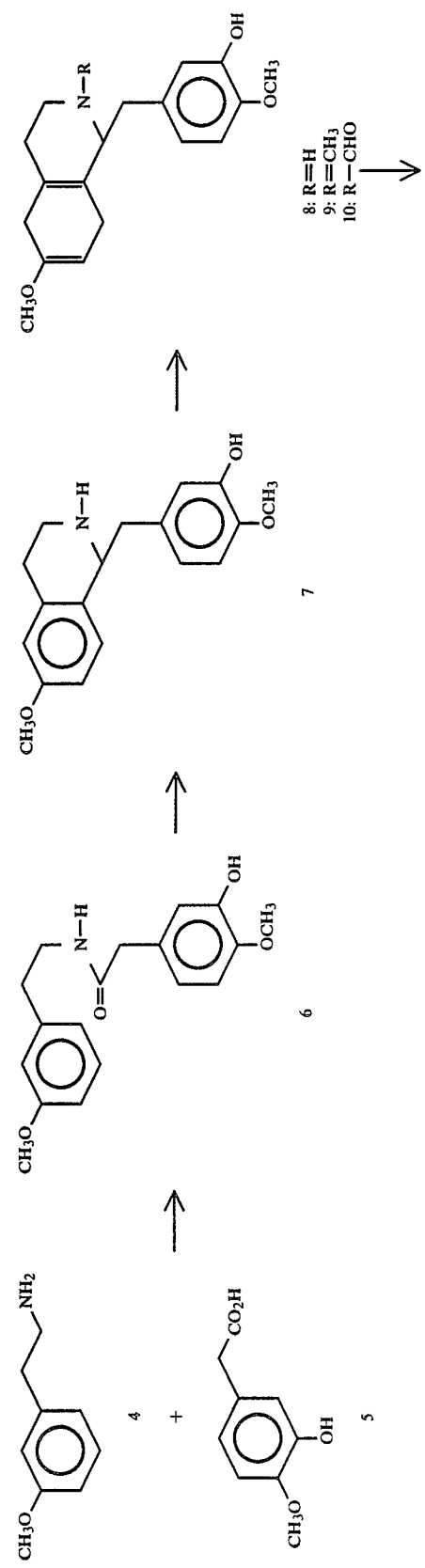

4,727,146
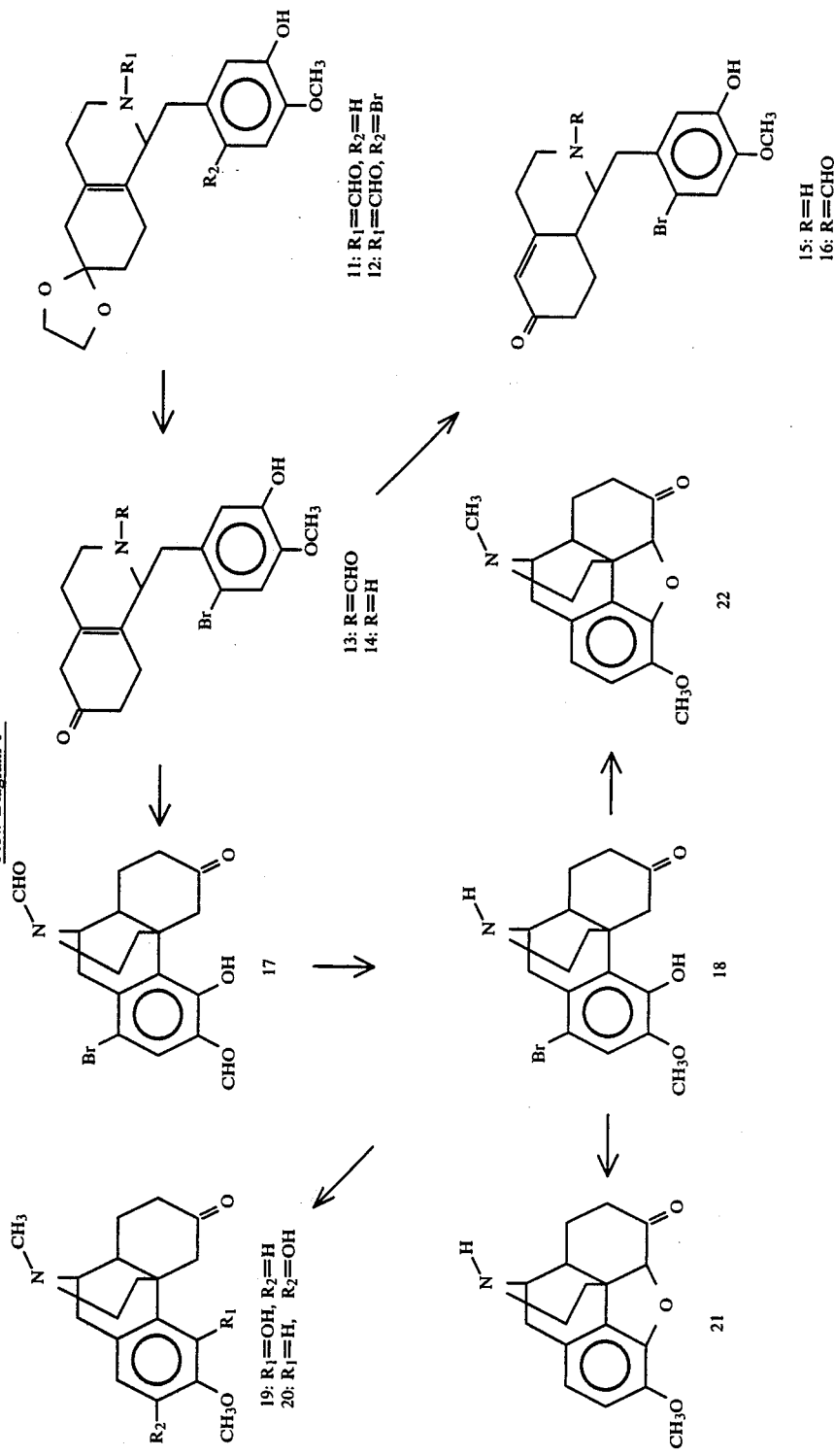
-continued
Flow Diagram 1

As a general summary of the above chart, the following general description is made commencing with codeine (1).

Racemic dihydrothebainone (19), nordihydrocodeinone (21) and dihydrocodeinone (22) were synthesized in high overall yield from 3-methoxyphenethylamine (4), via the key intermediate (±)-1-bromonordihydrothebainone (18); the route utilized unprotected phenolic intermediates, involved directed Grewe-type cyclization and for 21 and 22, exploited novel oxide bridge closure in the N-nor series.

Heating a mixture of amine (4) and pure acid (5) afforded amide (6). Cyclization of 6 generated an aqueous solution of the 1,2-dehydro derivative of 7, compound 4' shown in Flow Diagram 2. This derivative is the starting point for the novel asymmetric synthesis of this invention. (The possibility for resolution of racemic tetrahydroisoquinoline 7 is suggested in the grandparent application.) Birch reduction with lithium and ammonia afforded 8. Refluxing 8 with PhOCHO or chloral gave 10. A solution of 10 and ethylene glycol generated a solution of ketal 11 and subsequently bromoketal 12 was produced. Grewe-type cyclization produced 17. Refluxing 17 in MeOH-aqueous HCl yielded 18. 19 is available from 18 by hydrogenation in the presence of formaldehyde. Synthesis routes from 18 yield 19, 21, and 22. Specific details are found in the grandparent application (U.S. Pat. No.4,410,700), incorporated by reference. Both the (+)- and (-)-enantiomers of 19, 21, or 22 are available using methodology described in previous applications by K. C. Rice (U.S. Pat. No. 4,410,700, U.S. Ser. No. 476,830 filed Mar. 18, 1983, and U.S. Ser. No. 165,690 filed July 3, 1980).

Conversion of (−)-19, (−)-21 or (−)-22 to (−)-thebaine (3) and (−)-codeine (1) and facile 0-demethylation of the latter to (-)-morphine (2) provide a practical total synthesis of these natural alkaloids. In a similar manner, (+)-19, (+)-21, or (+)-22 afford unnatural (+)-thebaine, (+)-codeine, and (+)-morphine by total synthesis.

SUMMARY OF THE INVENTION

This invention relates to total and partial development or synthesis of morphinan compounds from isoquinolines, as is illustrated in Flow Diagrams 1 and 2.

In the development of this total synthesis of morphinans, one portion of the process relates to the use of asymmetric reduction, either catalytic or chemical. A definition of asymmetric reduction is as follows: Asymmetric reduction is a catalytic or chemical reduction process of a prochiral intermediate in which there is favored one isomer of paired optical isomers, either the (+)- or (−)- antipode. In the production of chiral morphinans by total synthesis, one of the key intermediates is a chiral 1-benzyl-1,2,3,4-tetrahydroisoquinoline. The precursor to this compound is a prochiral 3,4-dehydroisoquinoline, which in Rice U.S. Pat. No. 4,410,700 was reduced with sodium borohydride to give a racemic mixture of the (+) and (−) tetrahydroisoquinolines which were separated by the optical resolution.

The advantage the present invention holds over the production of these optical isomers of the tetrahydroisoquinolines by optical resolution is that when these compounds are produced by optical resolution, only 50% of the material can be obtained as a theoretical or maximum of the isomer desired because the racemic mixture contains an equal amount of the unwanted isomer. This necessitates recycling the unwanted isomer back to the racemic and then another optical resolution to obtain more of the desired tetrahydroisoquinoline, either the (+) or (−), depending on whether the object is to make the natural or the unnatural morphine derivatives.

A further aspect of the invention consists of asymmetric reduction of intermediates 4'–6' to give 1'–3'. For this reduction process either asymmetric catalytic or chemical reduction may be used.

For catalytic reduction, hydrogenation of 4'–6' using rhodium complexes with chiral ligands such as DI-PAMP, CHIROPHOS or NORPHOS (available from Reaction Design, Hillside, NJ) are used in alkanols, alkanol ethers, water or mixtures thereof. U.S. Pat. No. 3,849,480 describes asymmetric hydrogenation catalysts and process steps. These catalysts have been used quite successfully in asymmetric hydrogenation of azalactones to eventually afford optically active amino acids. Intermediates of the type 7'–9' which are easily available from 4'–6' by standard methods are ideal for asymmetric hydrogenation to the N-acetyl derivatives of 1'–3'. The 1'–3' can then be obtained by standard acid or alkaline hydrolysis of the acyl group(s) or the chiral N-acyl derivatives can be utilized directly for further reaction.

For chemical reduction of 4'–6' to 1'–3', chiral boranes such as diisopinocampheylborane derived from the readily available (+) and (−)-pinene and other chiral boranes may be employed in ether-type solvents such as tetrahydrofuran, glyme (dimethyl ether of ethylene glycol) and diglyme. Also, chemical reduction with sodium borohydride and sodium cyanoborohydride in reaction media such as aqueous or aqueous alcoholic chiral tartrate-phosphate buffer systems may be employed. By utilization of either (+) or (−)-tartaric, malic or other optical pairs of organic acid either enantiomer of 1'–3' may be obtained.

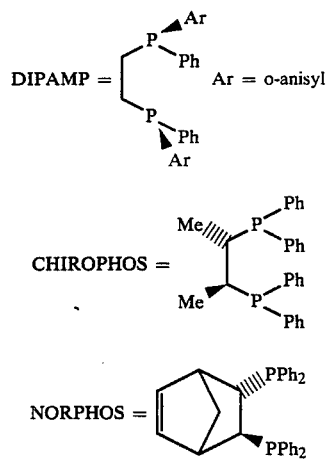

In the present invention, the desired isomer is produced exclusively, or nearly so, directly from the dehydroisoquinoline by process of chiral chemical or catalytic reduction. This eliminates the need to do the optical resolution in the first place and since only one isomer is produced, the racemization of the unwanted isomer and re-resolution is eliminated. Specially referring to Flow Diagram 2, this asymmetric hydrogenation by chiral hydrogenation catalyst or this asymmetric chemical reduction can be done on two compounds, either 4' through 6' or 7' through 9'. In the case of 7' through 9', these compounds are formed from 4' through 6' by treatment with lower acid anhydrides, such as acidic anhydride, and heat. This introduces an N-acyl substituent with migration of the double bond exocyclic from the 1 position to the benzylic position. This is the resulting compound 7' through 9', known as an enamide, and these compounds respond very favorably to asymmetric catalytic hydrogenation using the chiral catalyst produced from rhodium salts and chiral phosphines. This type of catalytic reduction of the enamide system present in 7' through 9' is also present in the azalactone route for production of L DOPA, which is utilized in a plant process of Hoffman-LaRoche to make L DOPA. This is the enamide system, although different compounds are used for the production of L DOPA. It is the enamide which is actually reduced to an L DOPA derivative which is then hydrolyzed to L DOPA. The compounds 4' through 6', the dihydroisoquinoline intermediates, can also be reduced using these chiral phosphine rhodium catalyst to produce either the (+) or (−) of tetrahydroisoquinoline intermediate. Chiral chemical reduction 4' through 6' can also be used. This involves utilization of chiral hydride containing reducing agents. In the Rice U.S. Pat. No. 4,410,700 the racemic tetrahydroisoquinoline was obtained by reduction of the dihydroisoquinoline with sodium borohydride. Since sodium borohydride is an achiral reducing agent of the racemic mixture was produced but with suitable organoboranes which are prepared from borane ($BH_3$) and optically active terpenes containing double bonds, then chiral will reduce the hydride reducing agents produced and can result in chiral reduction of the dihydroisoquinolines to either the (+) or the (−) tetrahydroisoquinoline. The chiral reduction of carbonyl containing compounds to alcohols with chiral borane reagents has been studied extensively by recent investigators using reagents derived from pinene and borane ($BH_3$) and others. In the reduction by catalytic hydrogenation with chiral catalyst of 7' through 9', the N-acyl tetrahydroisoquinoline (optically active tetrahydroisoquinoline), is produced, and then in the last step the N-acyl substituent is hydrolyzed either by alkaline or acid hydrolysis to give the chiral tetrahydroisoquinolines 1' through 3'. These compounds are obtained directly by chiral catalytic reduction or chiral chemical reduction of the dihydroisoquinoline intermediate 4' through 6'. This dihydroisoquinoline intermediate is the same 4' through 6' or the same intermediates which were obtained or were produced in the Rice U.S. Pat. No. 4,410,700. Compounds 5' and 6' are prepared by an analogous method. In a process involving the total synthesis of morphinans from isoquinolines, and more particularly these two, the hydrogenation of 8' and 9' to effect or to produce 2' and 3' and to produce the final compound, which is less the N-acyl group, utilizes a catalyst of chiral phosphine rhodium catalyst. Acid or alkaline hydrolysis of the N-acyl derivatives of compound 1'-3' gives 1'-3'. Another process would involve direct reduction of 4'-6' to 1'-3' with chiral phosphine rhodium catalyst. Another process would be chiral chemical reduction of compounds 4'-6' to produce compounds 1'-3'. Chiral chemical reduction is carried out with suitably modified sodium borohydride. The borohydride ion can be modified with an optically active amino acid to produce a triacyloxyborane which, with one hydride ion left, serves as the chiral reducing agent. This method of reduction has been described by the Tanabe Company for isoquinoline systems but not identical to the present invention to produce an enriched mixture of the chiral tetrahydroisoquinoline. Also, lithium aluminum hydride modified with chiral ephedrin, Darvon alcohol, or other amino alcohols can also be used.

EXAMPLE 1

Chiral Synthesis of 1'-3' from 4'-6' or 7'-9' by Asymmetric Hydrogenation

In a typical example for the reduction of the dihydroisoquinoline intermediate 4'-6', compound 4' can be reduced with methanol as a solvent and about 1% of a chiral catalyst prepared from rhodium III chloride and the asymmetric ligand known as DIOP (Kagan, et al, *J. Am. Chem. Soc.*, 94:6429, 1972; Dang, et al, *Journal Organomet. Chem.*, 91:105, 1975).

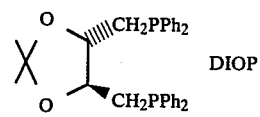

DIOP

The catalyst is prepared as a 0.1% solution in 1 liter of methanol. The catalyst is prepared by mixing approximately equal molar amounts of rhodium III chloride and the SS isomer of DIOP, a chiral phosphine ligand. The RR isomer of this compound is also available. The hydrogenation of this compound 4' is performed in about a 10% solution in methanol and the catalyst utilized is about 1% of the substrate reduced, so in 1000 ml of methanol, 100 grams of the compound 4 is reduced with about 1 gram of a chiral rhodium phosphine catalyst. The catalyst is prepared by treatment of a solution of rhodium III chloride in methanol which has been rigorously deoxygenated with an approximate molar equivalent of the chiral asymmetric catalyst DIOP. After preparation of the catalyst and stirring for 30 min. the 100 grams of compound 4' is added. The batch is stirred and hydrogenated at 1.1 atmospheres until approximately the calculated amount of hydrogen has been absorbed. An equal volume of water is then added to the reaction mixture and concentrated aqueous ammonia added at a fast drop rate to precipitate the chiral compound which is the crude (+)-isomer of the desired tetrahydroisoquinoline precursor. This compound is then suspended in methanol and treated with a slight excess of HCl gas or concentrated 37% HCl to precipitate the hydrochloride salt of the (+)- tetrahydroisoquinoline. This compound was found to be optically pure or very nearly so after recrystallization of the hydrochloride salt.

The catalytic hydrogenation can also be performed by replacing DIOP with a chiral phosphine ligand DICAMP (Knowles, et al, Ger. Offen. No. 2,456,937, June 26, 1975; CA 83:P164367q)

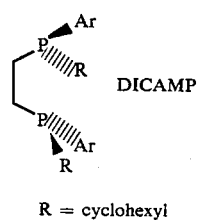

DICAMP

R = cyclohexyl

-continued

Ar = o-anisyl

The DIOP reagent is referred to ante. Both the S,S and the R,R isomers of the ligand DIOP procedures are noted for the preparation of these compounds and also the S,S and the R,R isomer of DICAMP.

This general hydrogenation procedure is applicable to the reduction of 5' and 6' to give the corresponding isomers of the corresponding tetrahydroisoquinoline. For hydrogenation of 7' to the O,N-diacyl derivative of tetrahydroisoquinoline 1', a similar procedure is followed. The hydrogenation is carried out in methanol at about the same concentration to give the chiral O,N-diacyl derivative of compound 1'. Acid or alkaline hydrolysis of the O,N-diacyl derivatives of the tetrahydroisoquinoline is performed to give the deacetylated tetrahydroisoquinoline. Using this procedure, and followed by purification of the hydrochloride salt as described, the material is obtained in near optical purity. Thus, this procedure renders either the (+) or the (−) tetrahydroisoquinoline available in good yield by hydrogenation of either the 4' or 7' type intermediates and using the appropriate isomer of the chiral phosphine ligand with rhodium salt, either the (+) or the (−) tetrahydroisoquinoline can be obtained.

EXAMPLE 2

Chiral Synthesis of 1'-3' from 4'-6' by Asymmetric Chemical Reduction

This general method is illustrated with compound 4'. The chiral reduction can be carried with several different chiral reducing agents. One of these chiral reducing agents can be prepared by stirring a slurry of sodium borohydride in tetrahydrofuran and treating with 3 moles of a N-acyl amino acid. One of the most desirable N-acyl amino acids for this is either (+) or (−) N-carbobenzoxyproline. The 3 molar equivalents of the proline derivative is stirred with the sodium borohydride until the evolution of hydrogen stops. This gives a triacyloxyborane derivative with 1 hydride ion remaining. This reagent is a functional asymmetric reducing agent and the reduction of compound 4' with this compound is carried out by adding compound 4' to a slight excess of the chiral reagent and stirring over night in tetrahydrofuran at 0° C. Evaporation of the tetrahydrofuran and treatment with a slight excess of aqueous hydrochloric acid regenerates the carbobenzoxy proline derivative which can be extracted out with ether. The hydrochloride of the chiral tetrahydroisoquinoline remains in the filtrate. Addition of equal volume of methanol followed by concentrated ammonium hydroxide pH 9 to 9.5 precipitates the chiral tetrahydroisoquinoline which can be isolated by filtration. Optical purity of the compound obtained in this manner is in the order of 85-90%.

The greatly enriched tetrahydroisoquinoline can be brought to optical purity by several crystallizations of the hydrochlroide salt or by crystallization as the tartrate followed by regeneration of the base and according to standard procedures.

In another type reaction, the chiral reducing agent can be prepared by treatment of sodium borohydride with either (+) or (−) tartaric acid. This gives a similar type of chiral reducing agent which is also effective in the reduction of compound 4' to the chiral tetrahydroisoquinoline.

Another way to accomplish this assymetric reduction of compound 4' to optically active tetrahydroisoquinolines is to reduce the compound in tetrahydrofuran with the reagent which is obtained by reacting 2 moles of optically active alpha pinene with borane in tetrahydrofuran. The solution of the diisopinocampheylborane functions as the reducing agent in the reduction of the intermediate 4' to chiral tetrahydroisoquinoline. Basically, the compound 4' is treated with a slight excess of this reagent produced from optically active pinene and $BH_3$ in tetrahydrofuran followed by evaporation and treatment with HCl which decomposes a complex and gives the hydrochloride of the tetrahydroisoquinoline in the aqueous phase. The base can then be recovered from the aqueous phase by treatment with ammonia and methanol as above.

The yield in this reaction is about 75% of material, which is about 85% optically pure. This material can then be purified by recrystallization of the hydrochloride salt a number of times or preferably by isolation as a tartrate salt in recrystallization. The optically active tetrahydroisoquinoline is then obtained by the standard isolation procedure from the salt.

Among the asymmetric reagents for chemical reduction which are useful in the reaction discussed above are lithium aluminum hydride modified with chiral ephedrin or (2S,3R)-(+)-4-dimethylamino-3- methyl-1,2-diphenyl-2-butanol (Darvon alcohol), or the antipode of the latter. Chiral B-3-pinanyl-9-borabicyclo[3.3.1]-nonane, monoisopinocampheylborane, di-3-pinanylborane, and lithium B-isopinocampheyl-9-borabicyclo[3.3.1]nonyl hydride are also useful in this reduction.

Flow Diagram 2

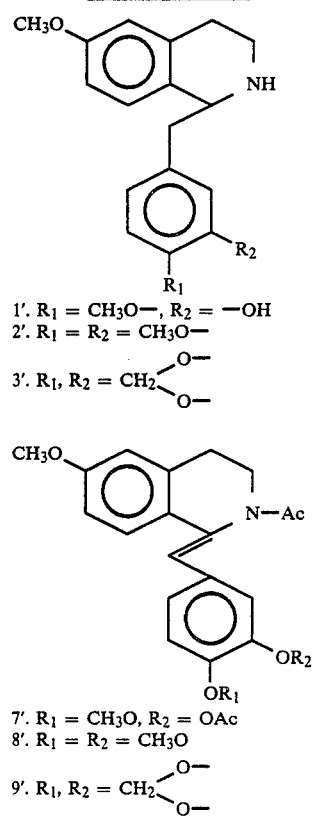

1'. $R_1 = CH_3O—$, $R_2 = —OH$
2'. $R_1 = R_2 = CH_3O—$
3'. $R_1, R_2 = CH_2\overset{O—}{\underset{O—}{\diagdown}}$ 7'. $R_1 = CH_3O$, $R_2 = OAc$
8'. $R_1 = R_2 = CH_3O$
9'. $R_1, R_2 = CH_2\overset{O—}{\underset{O—}{\diagdown}}$ -continued
Flow Diagram 2

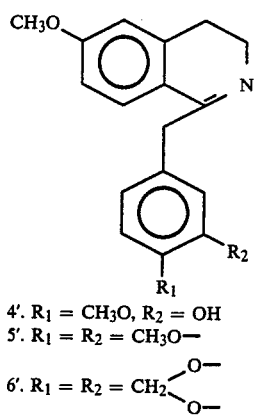

4'. R₁ = CH₃O, R₂ = OH
5'. R₁ = R₂ = CH₃O—
6'. R₁ = R₂ = CH₂⟨O—/O—⟩

I claim:
1. A method of chiral reduction of a compound selected from dihydro 4', 5' or 6' or 7', 8' or 9', which are all dihydroisoquinolines, to chiral tetrahydroisoquinolines 1', 2', 3' utilizing either (a) asymmetric chemical reduction with borane modified with (+) or (−) alpha or beta pinene or sodium borohydride modified with (+) or (−)-N-carbobenzoxy aminoacids, or sodium borohydride modified with (+) or (−)-tartaric acids, or lithium aluminum hydride modified with (+) or (−)-ephedrine or (+) or (−)-darvon alcohol or (b) asymmetric catalytic reduction using a chiral rhodium complex of

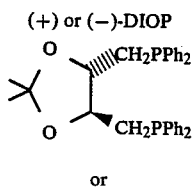
(+) or (−)-DIOP or (+) or (−)-DIPAMP

-continued

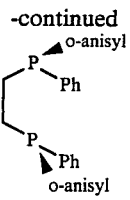

and set out as follows:

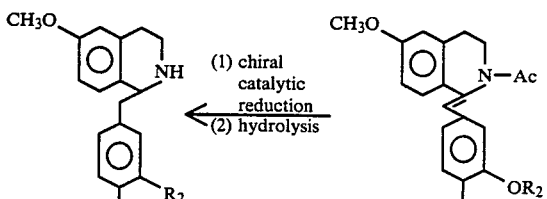

1'. R₁ = CH₃O—, R₂ = —OH
2'. R₁ = R₂ = CH₃O—
3'. R₁, R₂ = CH₂⟨O—/O—⟩

7'. R₁ = CH₃O, R₂ = OAc
8'. R₁ = R₂ = CH₃O
9'. R₁, R₂ = CH₂⟨O—/O—⟩

Ac = lower acyl

↑ chiral chemical reduction        Ac₂O ↗

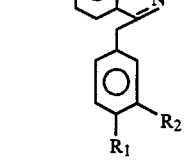

4'. R₁ = CH₃O, R₂ = OH
5'. R₁ = R₂ = CH₃O—
6'. R₁ = R₂ = CH₂⟨O—/O—⟩

* * * * *